United States Patent
Stever et al.

(10) Patent No.: US 9,795,743 B2
(45) Date of Patent: Oct. 24, 2017

(54) DRIVE ASSEMBLY FOR A MEDICATION DELIVERY DEVICE AND MEDICATION DELIVERY DEVICE COMPRISING A DRIVE ASSEMBLY

(71) Applicant: SANOFI-AVENTIS DEUTSCHLAND GMBH, Frankfurt am Main (DE)

(72) Inventors: Tobias Stever, Frankfurt am Main (DE); Peter Heilig, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 346 days.

(21) Appl. No.: 14/353,522

(22) PCT Filed: Nov. 8, 2012

(86) PCT No.: PCT/EP2012/072080
§ 371 (c)(1),
(2) Date: Apr. 23, 2014

(87) PCT Pub. No.: WO2013/068435
PCT Pub. Date: May 16, 2013

(65) Prior Publication Data
US 2014/0303566 A1    Oct. 9, 2014

(30) Foreign Application Priority Data
Nov. 9, 2011  (EP) ..................... 11188466

(51) Int. Cl.
*A61M 5/315*    (2006.01)
*A61M 5/24*     (2006.01)

(52) U.S. Cl.
CPC .... *A61M 5/31501* (2013.01); *A61M 5/31543* (2013.01); *A61M 5/24* (2013.01);
(Continued)

(58) Field of Classification Search
CPC .......... A61M 5/31501; A61M 5/31543; A61M 2005/2407; A61M 5/31551; A61M 5/24;
(Continued)

(56) References Cited

U.S. PATENT DOCUMENTS 5,578,015 A    11/1996  Robb
6,419,656 B1    7/2002  Vetter et al.
(Continued)

FOREIGN PATENT DOCUMENTS

CN          102083489 A      6/2011
DE    WO 2010063687 A1 *    6/2010    ........ A61M 5/31505
(Continued)

OTHER PUBLICATIONS

Chinese Office Action for CN Application No. 201280055370.4, dated Sep. 25, 2015.
(Continued)

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A drive assembly for a medication delivery device is provided, comprising a piston rod which is movable from a start position to an end position for medication delivery and resettable from the end position to the start position. The drive assembly further comprises an impeding element for impeding a movement of the piston rod from the end position to the start position during a reset of the piston rod, wherein the impeding element comprises at least one resilient element. Furthermore, a medication delivery device comprising the drive assembly is disclosed.

13 Claims, 4 Drawing Sheets

(52) U.S. Cl.
CPC ..... *A61M 5/31551* (2013.01); *A61M 5/31585* (2013.01); *A61M 2005/2407* (2013.01); *A61M 2005/3151* (2013.01)

(58) Field of Classification Search
CPC ...... A61M 5/31585; A61M 2005/3151; A61M 5/31505; A61M 2005/31506; A61M 5/31506
See application file for complete search history.

(56) References Cited

U.S. PATENT DOCUMENTS

| | | | | |
|---|---|---|---|---|
| 2008/0119796 | A1* | 5/2008 | Graf | A61M 5/315 604/207 |
| 2009/0275916 | A1* | 11/2009 | Harms | A61M 5/24 604/506 |
| 2014/0081238 | A1 | 3/2014 | Bendek et al. | |

FOREIGN PATENT DOCUMENTS

| | | |
|---|---|---|
| EP | 0594349 | 4/1994 |
| GB | 551545 | 2/1943 |
| JP | 2008-521494 A | 6/2008 |
| WO | 2006/058061 A1 | 6/2006 |
| WO | 2007/020090 | 2/2007 |
| WO | 2009/132778 | 11/2009 |
| WO | 2010/063687 | 6/2010 |
| WO | 2010/115817 A1 | 10/2010 |

OTHER PUBLICATIONS

International Search Report for Int. App. No. PCT/EP2012/072080, dated Dec. 5, 2012.
Japanese Office Action for JP Application No. 2014-540445, dated Aug. 23, 2016.

* cited by examiner

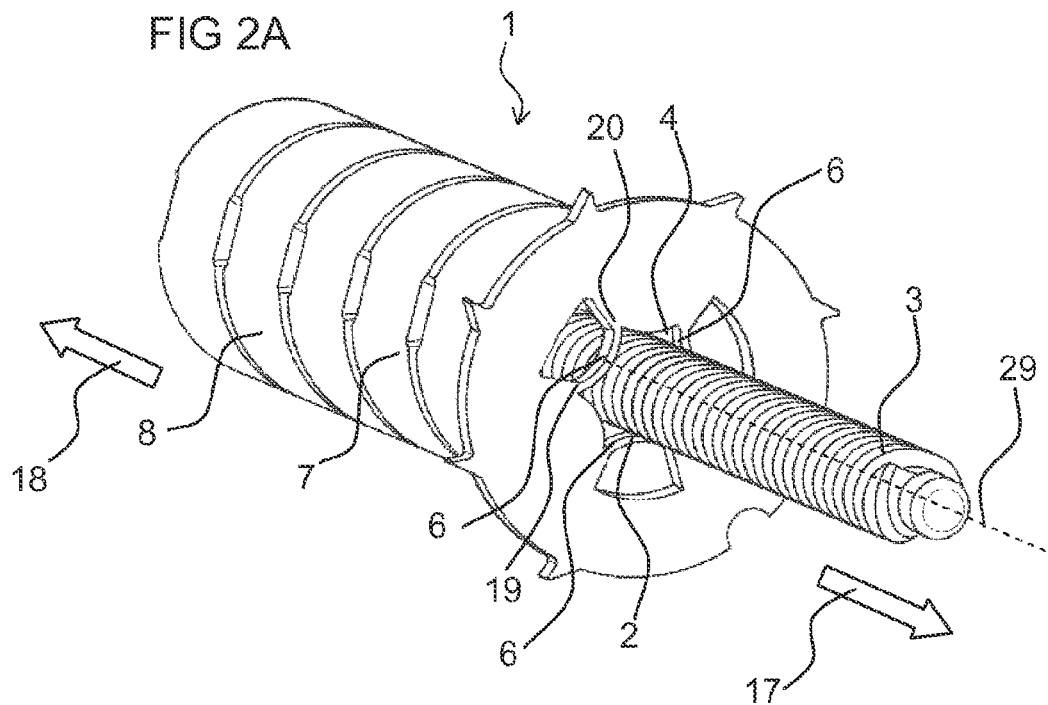
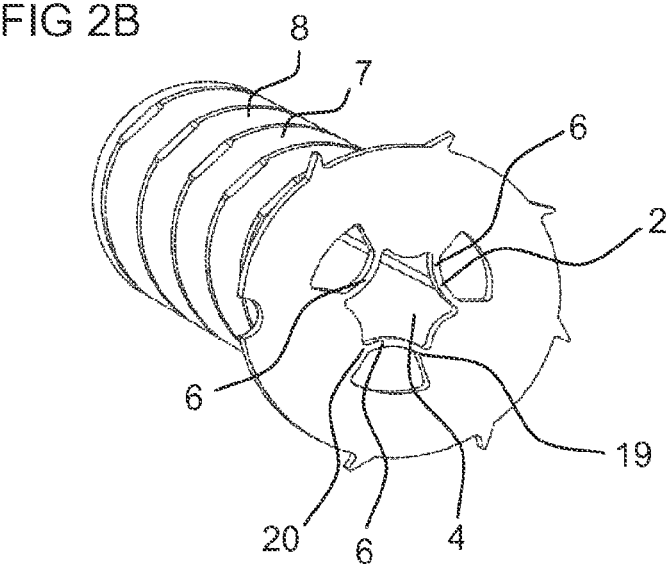

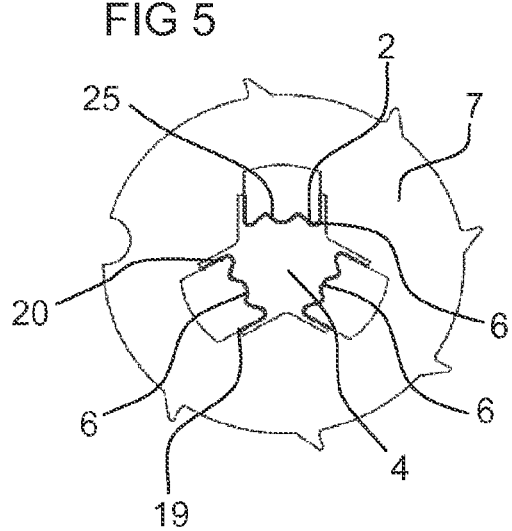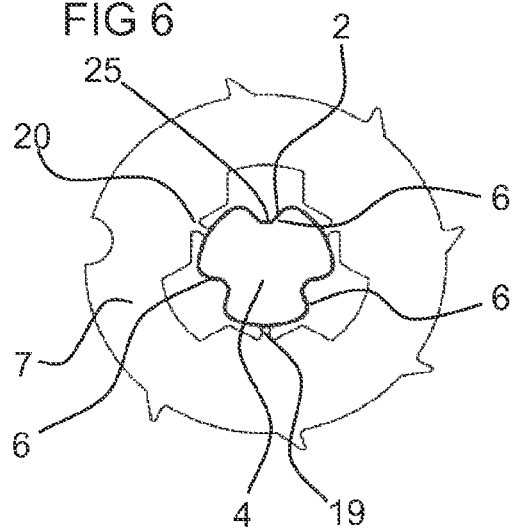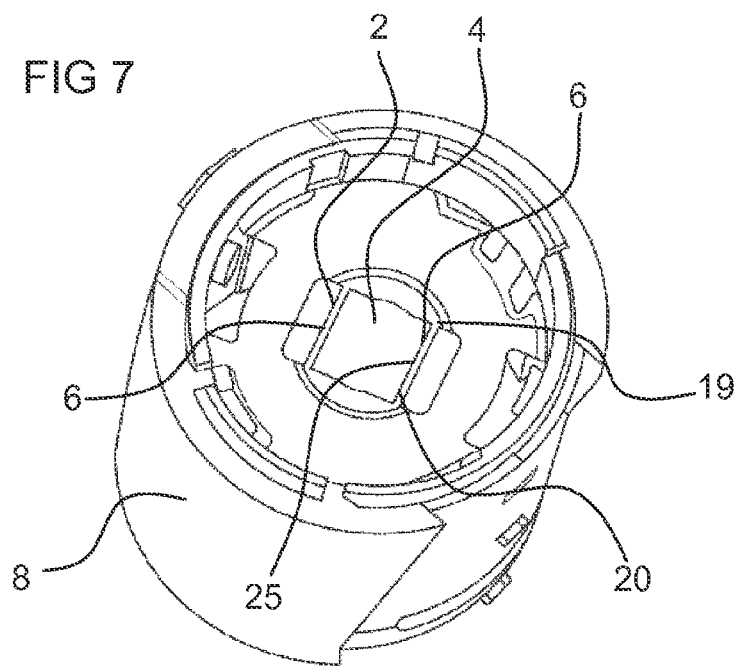

DRIVE ASSEMBLY FOR A MEDICATION DELIVERY DEVICE AND MEDICATION DELIVERY DEVICE COMPRISING A DRIVE ASSEMBLY

CROSS REFERENCE TO RELATED APPLICATIONS

The present application is a U.S. National Phase Application pursuant to 35 U.S.C. §371 of International Application No. PCT/EP2012/072080 filed Nov. 8, 2012, which claims priority to European Patent Application No. 11188466.4 filed Nov. 9, 2011. The entire disclosure contents of these applications are herewith incorporated by reference into the present application.

TECHNICAL FIELD

The present disclosure relates to a drive assembly for a medication delivery device.

BACKGROUND

A medication delivery device comprising a drive assembly is known from patent application WO 2009/132778 A1. This application relates to a medication delivery device comprising a multi-dose medication cartridge, which can be replaced when the medication has been fully dispensed.

SUMMARY

It is an object of the present invention to provide a drive assembly for a medication delivery device having improved properties.

According to one aspect of the disclosure, a drive assembly for a medication delivery device is provided. The drive assembly comprises a piston rod which is movable from a start position to an end position for medication delivery and resettable from the end position to the start position. Furthermore, the drive assembly comprises an impeding element, wherein the impeding element comprises at least one resilient element. The impeding element may be configured to impede a movement of the piston rod from the end position to the start position during a reset of the piston rod.

The term "piston rod" is preferably used for a component of a drive assembly, which is configured to carry out a movement towards a dispensing end of a medication delivery device and, thereby, cause a medication to be dispensed from the device. In particular, a movement from the start position to the end position may correspond to a movement towards the dispensing end.

The start position may be a position of the piston rod wherein the piston rod is furthest away from the dispensing end of the device when the drive assembly is assembled with the medication delivery device. The end position may be a position wherein the piston rod is closest to the dispensing end of the medication delivery device. Accordingly, a movement from the end position to the start position may be a movement in the proximal direction. The "proximal direction" is a direction towards the proximal end of the medication delivery device. The term "proximal end" designates that end of the device which is or is to be arranged furthest away from a dispensing end of the device. A movement from the start position to the end position, for example during the delivering of a medication, may be a movement in a distal direction. The "distal direction" is a direction towards the dispensing end of the medication delivery device.

The piston rod may be configured to act on a bung or a piston in a medication container, for example a cartridge, causing a medication to be dispensed from the container. The piston rod may be configured for carrying out a combined axial and rotational movement. As an example, the piston rod may be configured as a simple rod. Preferably, the piston rod is configured as a lead screw. The lead screw may comprise threaded sections for engaging with corresponding parts of the medication delivery device. Preferably, the piston rod comprises at least one threaded section.

In a preferred embodiment, the drive assembly may be used in an injection device. Preferably, the medication delivery device may be a pen-type device. The medication delivery device may be configured to deliver a medical fluid. In particular, the medication may be insulin.

The piston rod may be configured to be reset to the start position when the medication from the cartridge has been partially or fully dispensed. By resetting the piston rod, the medication delivery device may be prepared for the insertion of a new cartridge, after the used cartridge has been replaced.

To enable a reset of the piston rod, a receptacle which may be attached to a main body of the medication delivery device may have to be detached from the main body. By the detachment of the receptacle, the piston rod may be enabled to be moved towards the start position. In particular, the drive assembly may comprise a locking device. The locking device may be configured to inhibit a movement of the piston rod towards the start position when the receptacle is attached to the main body. When the receptacle is detached from the main body, the locking device may be disengaged from the main body. Thereby, the piston rod may be enabled to be moved towards the start position.

Particularly, the piston rod may be rotated back to the start position. In particular, the piston rod may carry out a combined rotational and linear movement. In a further embodiment, the movement of the piston rod may be linear and a rotational movement may be prevented.

Preferably, the impeding element inhibits an unhindered movement of the piston rod from the end position to the start position. In particular, an unhindered movement of the piston rod may be inhibited when the receptacle is removed from the main body of the medication delivery device. Particularly, the resilient element may be configured to inhibit a movement of the piston rod when the receptacle is removed from the main body of the medication delivery device unintended, for example a movement caused by a gravitational force of the piston rod may be inhibited. Preferably, the impeding element is coupled to the piston rod such that the piston rod may only be moved back to its start position against a resistance, in particular a friction force exerted on the piston rod by the resilient element. Preferably, the impeding element slides along the piston rod during a reset of the piston rod. The impeding element may be not in engagement with engagement means of the piston rod. In particular, the impeding may be not in engagement with a threaded section of the piston rod and may slide over the threaded section of the piston rod at least during the reset of the piston rod. Preferably, the impeding element is configured such that the piston rod may still be moved back to its start position by a user without difficulty.

In particular, the resilient element may be configured to be in contact with the piston rod such that a movement of the piston rod may be impeded.

The impeding element may comprise a biasing element. Preferably, the biasing element is pre-tensioned towards the piston rod. In particular, the resilient element may be configured as a biasing element or may comprise a biasing element. The biasing element may comprise a spring element, for example a bias spring.

Preferably, during a movement of the piston rod, the impeding element exerts a friction force on the piston rod. The friction force may be exerted on the piston rod at least during a movement from the end position to the start position. The friction force may also be exerted on the piston rod during a movement from the start position to the end position. Preferably, the friction force does not lead to a significant increase of the force required for the delivery of a medication.

The amount of the friction force may be adjusted by adjusting the elasticity of the resilient element. In particular, the amount of the friction force may be increased by decreasing the elasticity of the resilient element. The amount of the friction force may be decreased by increasing the elasticity of the resilient element.

In a preferred embodiment, the drive assembly is configured such that the impeding element exerts a radial force on the piston rod. In particular, the resilient element may exert a radial force on the piston rod.

The amount of the radial force may be adjusted by adjusting the elasticity of the resilient elements.

In a preferred embodiment, the impeding element comprises a plurality of resilient elements. The plurality of resilient elements may be configured as biasing elements. Preferably, the resilient elements are located rotationally symmetric around the piston rod.

Preferably, the resilient elements are arranged at the same axial position relative to a longitudinal axis of the drive assembly. As an example, the impeding element may comprise three resilient elements being arranged at an angular distance of 120° relative to each other. The resilient elements may be arranged such that the piston rod is uniformly loaded along its circumference.

Furthermore, the impeding element may comprise at least one support bearing. As an example, the impeding element may comprise at least one resilient element exerting a force on the piston rod and at least one support bearing supporting the piston rod against the force exerted by the resilient element. In particular, the resilient element may comprise a biasing element, for example a spring element. For example, the impeding element may comprise two support bearings and one biasing element, which are located at an angular distance of 120° relative to each other. The support bearings may support the piston rod in a direction such that a radial position of the piston rod is maintained. In particular, the position of the piston rod may be centred in the drive assembly.

Preferably, the drive assembly comprises a member forming an opening. The piston rod may extend through the opening. Preferably, the piston rod is arranged concentric in the opening. Preferably, the impeding element is located at the opening.

In an exemplary embodiment of the medication delivery device, the piston rod may extend through several openings of different members of the drive assembly.

Preferably, the impeding element is configured to extend into the opening.

Thereby, the distance between the piston rod and an edge of the opening may be bridged by the impeding element. The distance between the piston rod and the edge of the opening may be bridged such that the impeding element is in direct contact with the piston rod.

Preferably, the impeding element is configured to be an integral part of the member forming the opening in the drive assembly.

Preferably, the member comprising the impeding element is injection moulded.

In an exemplary embodiment, the impeding element may comprise at least one support bearing.

The support bearing may be located at the opening of the member of the drive assembly. The support bearing may be configured to support the piston rod against a force exerted on the piston rod by the resilient element and, thus, exert a counterforce on the piston rod. In particular, the support bearing may exert a force on the piston rod in a direction which is at least partially opposed to the direction of force exerted on the piston rod by the resilient element. In particular, the support bearing may be provided in the case that only a single resilient element is provided. Thereby, the piston rod may be uniformly loaded by the resilient element and the support bearing. Additionally or alternatively, the support bearing may be provided in the case that a plurality of resilient elements is located rotationally asymmetric around the piston rod. The at least one support bearing may support the piston rod in a direction such that a radial position of the piston rod is maintained. Additionally, the support bearing may guide the piston rod in an axial direction.

In a preferred embodiment, the drive assembly comprises a dose-limiting member being configured to prevent a setting of a dose of medication which is larger than a maximal available amount of medication in a cartridge. Additionally or alternatively, the dose-limiting member may be configured to prevent a movement of the piston rod in a distal direction when the piston rod has reached its end position.

In an exemplary embodiment, the member forming the opening may be the dose limiting member.

In a preferred embodiment, the impeding element is configured to be an integral part of the dose-limiting member.

The dose-limiting member may comprise an opening. Preferably, the piston rod extends through the opening. In a preferred embodiment, the impeding element is located at the opening of the dose-limiting member, such that the impeding element extends into the opening of the dose-limiting member. In particular, the resilient element may extend into the opening of the dose-limiting member.

In a preferred embodiment, the impeding element comprises a clamp.

The clamp may be configured to clamp the piston rod. Preferably, the clamp may clamp the piston rod such that an unhindered movement of the piston rod is inhibited. In particular, the clamp may lead to an increase of the friction force acting on the piston rod during a movement of the piston rod towards its start position. For example, the piston rod may be clamped between several resilient elements.

In a preferred embodiment, the resilient element may comprise two ends. In an exemplary embodiment, both ends of the resilient element may be connected to a member of the drive assembly, in particular a member forming an opening in the drive assembly. In this case, high mechanical stability of the resilient element may be achieved.

In a further embodiment, only one end of the resilient element may be connected to a member of the drive assembly. Thereby, the elasticity of the resilient element may be increased. Moreover, a high range of tolerances may be covered. In particular tolerances between the piston rod and the resilient element may be compensated. Furthermore, by connecting only one end of the resilient element to the member, the friction force acting on the piston rod may be decreased. In particular, the radial force exerted on the piston rod may be reduced compared to a resilient element being connected to a member of the drive assembly at both ends.

In one embodiment, the impeding element may comprise the shape of a meander. In particular, the resilient element may comprise the shape of a meander. For example, the resilient element may be waved. Thereby, both a high stability and a high elasticity may be achieved.

In a further embodiment, the impeding element may comprise the shape of an arch. In particular, the resilient element may comprise the shape of an arch.

In a further embodiment, the impeding element may comprise a straight shape. Particularly, the resilient element may comprise a straight shape.

According to a further aspect of the present disclosure, a medication delivery device is provided, the medication delivery device comprising the drive assembly. The drive assembly may comprise any structural and functional features as described above. The medication delivery device may be an injection device. Preferably, the medication delivery device is a pen-type device. Preferably, the medication delivery device is configured to dispense a medication, in particular a medical fluid. Particularly, the medication may be insulin. Preferably, the medication delivery device is a reusable device.

The medication delivery device may comprise a medication receptacle being configured to receive a cartridge containing a medicament.

In a preferred embodiment, the medication delivery device comprises a main body, wherein the receptacle may be detachable from the main body to enable an exchange of the cartridge. In particular, a used cartridge may be removed and a new one may be inserted. Preferably, when the receptacle is detached, a reset of the piston rod to the start position is enabled. The piston rod may have to be in the start position when a medication receptacle holding a new cartridge is attached to the main body. The piston rod may be in the end position when the medication from the cartridge has been fully delivered.

Preferably, the impeding element is configured to inhibit an unhindered resetting of the piston rod when the receptacle is detached from the main body. Particularly, the impeding element may be configured to inhibit an unhindered movement of the piston rod from the end position to the start position when the receptacle is detached from the main body. In particular, an accidental movement of the piston rod may be prevented. As an example, an unintended movement of the piston rod during an accidental detachment of the receptacle may be prevented.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2, H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

BRIEF DESCRIPTION OF THE FIGURES

FIG. 2A shows a perspective view of an exemplary embodiment of a drive assembly for a medication delivery device.

FIG. 2B shows the embodiment of FIG. 2A without showing the piston rod.

FIG. 5 shows a front view of a fourth embodiment of a drive assembly for a medication delivery device.

FIG. 6 shows a front view of a fifth embodiment of a drive assembly for a medication delivery device.

FIG. 7 shows a perspective view of a sixth embodiment of a drive assembly for a medication delivery device.

Like elements, elements of the same kind and identically acting elements may be provided with the same reference numerals in the figures.

DETAILED DESCRIPTION

Figure 1:
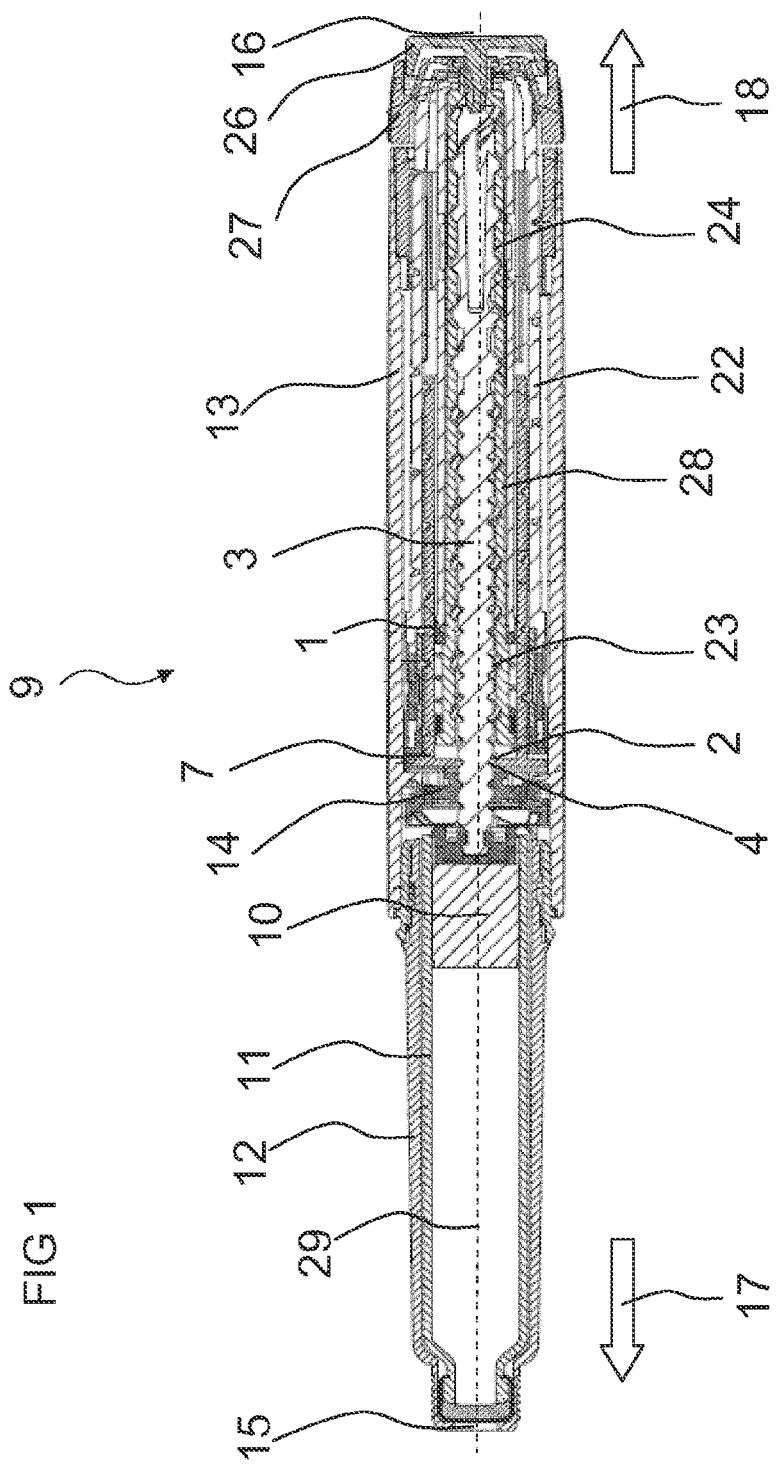
FIG. 1 shows a cross-sectional view of a medication delivery device comprising a drive assembly.

FIG. 1 shows a medication delivery device 9, in particular an injection device. For the detailed description of the medication delivery device 9 it is referred to WO 2009/132778 A1. The medication delivery device 9 comprises a drive assembly 1 comprising a piston rod 3.

The piston rod 3 acts on a piston 10 in a cartridge 11 containing a medication. The cartridge 11 is located in a receptacle 12. The receptacle 12 is attached to a main body 13 of the medication delivery device 9.

The piston rod 3 is configured as a lead screw. The lead screw comprises two threaded sections 23, 24. A first threaded section 23 is located at a distal part of the piston rod 3 and a threaded section 24 is located at a proximal part of the piston rod 3. The piston rod 3 is in threaded engagement with a nut member 14 with the first threaded section 23. Furthermore, the piston rod 3 is in threaded engagement with a drive member 28 with the second threaded section 24. The drive member 28 exerts a force on the piston rod 3 to cause a movement of the piston rod 3 for a dose delivery operation. The threaded sections 23, 24 have opposite senses of rotation.

The medication delivery device comprises a dose setting member 22 and a dispense button 26. For setting a dose, the dose setting member 22 is rotated until the desired dose has been reached. The dose setting member 22 comprises a dial grip 27. By rotating the dial grip 27, the dose setting member 22 is rotated. For dispensing the set dose, the dispense button 26 is depressed.

Furthermore, the medication delivery device 9 comprises a dose limiting member 7. The dose limiting member 7 is configured to inhibit the setting of a dose which is larger than a maximal available amount of medication.

For delivering a dose of a medication, the piston rod 3 is moved in a distal direction 17, towards a distal end 15 of the medication delivery device 9. The distal end 15 is the dispensing end of the medication delivery device 9.

In the depicted embodiment the piston rod 3 is shown in a start position. During the delivery of a dose of a medication, the piston rod 3 is moved towards an end position. The start position may be the most proximal position of the piston rod 3. The end position may be the most distal position of the piston rod 3. In particular, the piston rod 3 may have reached the end position when the medication of a cartridge 11 has been fully or partially delivered.

In particular, during dose delivery, the piston rod 3 is rotated towards a distal end 15 through a nut member 14 for delivering a dose of medication.

The piston rod 3 may be moved in a proximal direction 18, towards a proximal end 16 of the medication delivery device 9 during a reset of the piston rod 3.

The medication delivery device 9 comprises a locking device for preventing a movement of the piston rod 3 in a proximal direction when the receptacle 12 is attached to the main body 13. In particular, the nut member 14 is rotationally fixed with respect to the main body 13 when the receptacle 12 is attached. Thereby, a movement of the piston rod 3 in a proximal direction may be inhibited due to a blocking by the two threaded sections 23, 24 being in engagement with the locking device comprising the nut member 14 and the drive member 28. When the receptacle 12 is detached from the main body 13 the nut member 14 may be disengaged from the main body 13, such that a rotation of the nut member 14 is enabled. Thereby, a reset of the piston rod 3 back to the start position is enabled. During a reset of the piston rod 3, the piston rod 3 rotates towards the proximal end 15. In particular, the piston rod 3 rotates through the dose setting member 22.

The drive assembly 1 comprises an impeding element 2 for impeding an unintended movement of the piston rod 3 during a detachment of the receptacle 12. The impeding element 2 is located at a member forming an opening through which the piston rod 3 extends. In the shown embodiment, the impeding element is located at the dose limiting member 7. In further embodiments, the impeding element 2 may be located at a different member of the drive assembly 1.

In particular, the impeding element 2 is configured to impede the movement of the piston rod 3 towards the start position. In particular, the impeding element is configured to exert a friction force on the piston rod 3. Thereby, an unhindered movement of the piston rod 3 towards the start position is inhibited.

FIGS. 2A to 7 show different embodiments of impeding elements.

FIG. 2A shows an exemplary embodiment of a drive assembly 1 for a medication delivery device. The drive assembly 1 may be used in the medication delivery device as shown in FIG. 1.

The drive assembly 1 comprises a member 8 forming an opening 4 and a piston rod 3 extending through the opening 4. The member 8 may correspond to the dose limiting member 7 shown in FIG. 1.

An impeding element 2 is located at the member 8. The impeding element 2 is configured to be in contact with the piston rod 3. In particular, the impeding element 2 impedes a movement of the piston rod 3 such that a force required for resetting the piston rod 3 to a start position is increased. In particular, the impeding element 2 is configured such that it exerts a radial force on the piston rod 3. Thereby, the piston rod 3 has to be moved against a resistance when resetting the piston rod 3. In particular, the impeding element 2 exerts a friction force on the piston rod 3.

The impeding element 2 may be an integral part of the member 8 of the drive assembly 1.

The impeding element 2 comprises at least one resilient element 6. In the depicted embodiment, the impeding element 2 comprises three resilient elements 6. Each resilient element 6 comprises a shape of an arch. The resilient elements 6 are in contact with the piston rod 3 such that the friction force acting on the piston rod 3 occurring during a reset of the piston rod 3 is increased. The resilient elements 6 are arranged rotationally symmetric around the piston rod 3. The resilient elements 6 are arranged at the same axial position relative to a longitudinal axis 29 of the medication delivery device.

The impeding element 2 is located at the opening 4 of the member 8 through which the piston rod 3 extends. The impeding element 2 extends into the opening 4. In particular, the resilient elements 6 extend into the opening. The resilient elements 6 comprise two ends 19, 20. The resilient elements 6 are connected to the opening 4 at both of their ends 19, 20. Thereby, a high stability of the resilient element 6 may be achieved.

FIG. 2B shows the embodiment of FIG. 2A without showing the piston rod.

Figure 3:
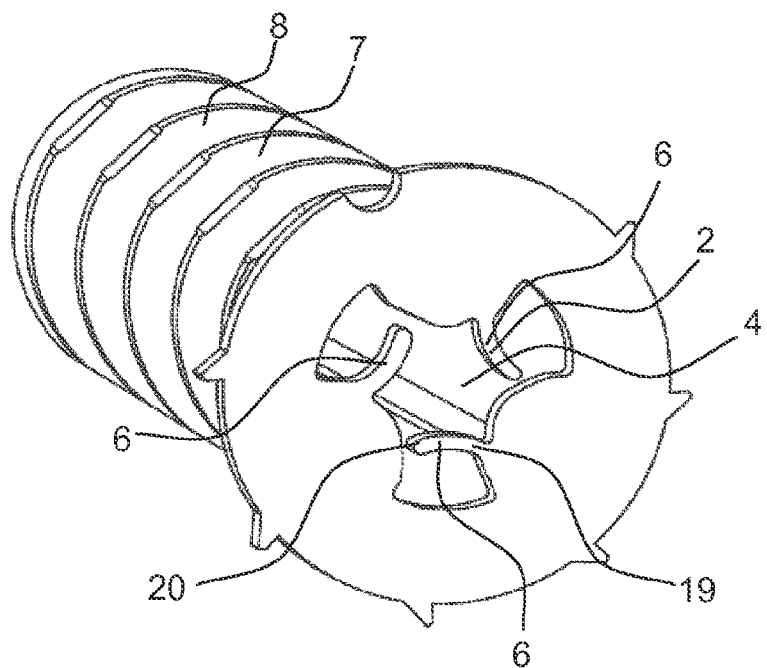
FIG. 3 shows a perspective view of a second embodiment of a drive assembly for a medication delivery device.

FIG. 3 shows a second embodiment of a drive assembly 1 for a medication delivery device. For clarity reasons, the piston rod is not depicted. This embodiment is similar to the embodiment shown in FIGS. 2A and 2B. The drive assembly 1 comprises an impeding element 2, which comprises three resilient elements 6. However, here, the resilient elements 6 are connected to the member 8 only at one of their ends 19. The other end 20 freely protrudes towards the piston rod 3. Thereby, the elasticity of the resilient element 6 may be increased, compared to the embodiment of FIGS. 2A and 2B. The resilient elements 6 may be elastically deformed by the piston rod 3 more easily because of the one-ended connection. Thereby, a radial force, which is exerted on the piston rod 3 by the resilient element 6, may be reduced.

Particularly, the friction force which occurs during the reset of the piston rod 3 may be decreased. Thereby, the required force for resetting the piston rod 3 exerted by a user may be reduced.

Figure 4:
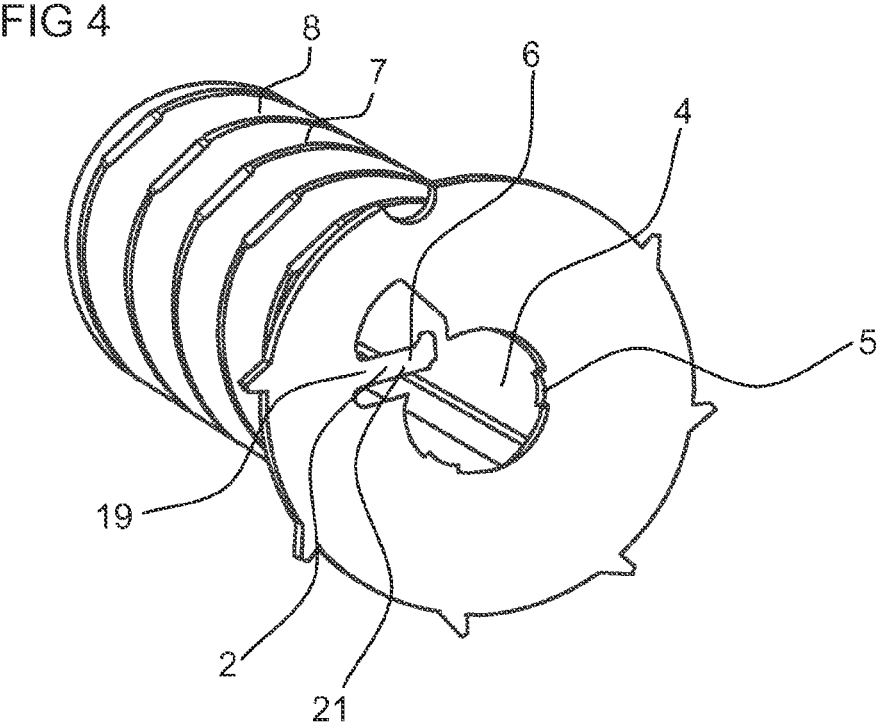
FIG. 4 shows a perspective view of a third embodiment of a drive assembly for a medication delivery device.

FIG. 4 shows a third embodiment of a drive assembly 1 for a medication delivery device. For clarity reasons, the piston rod is not depicted. The drive assembly 1 comprises an impeding element 2 which comprises a resilient element 6 comprising a spring arm 21. The spring arm 21 is pre-tensioned towards the piston rod 3. Accordingly, the spring arm 21 is configured as a biasing element. Thereby, the spring arm 21 exerts a radial force on the piston rod 3. The spring arm 21 comprises the shape of a hook. Thereby, the contact area between the piston rod 3 and the resilient element 6 is increased. The spring arm 21 is connected to the member 8 at one end 19. Thereby, a high elasticity of the resilient element 6 may be achieved.

Furthermore, the impeding element 2 comprises two support bearings 5. The support bearings 5 are configured such that they may support the piston rod 3 when the spring arm 21 exerts a force on the piston rod 3. The support bearings 5 are located at the opening 4 of the member 8. Particularly, the support bearings 5 support the piston rod 3 in a direction such that a radial position of the piston rod 3 is maintained. In particular, the position of the piston rod 3 is maintained concentric in the opening 4 of the member 8.

FIG. 5 shows a fourth embodiment of a drive assembly 1 for a medication delivery device. For clarity reasons, the piston rod is not depicted. The drive assembly 1 comprises an impeding element 2 comprising three resilient elements 6. The resilient elements 6 of the impeding element 2 comprise a meander shape. Particularly, the resilient elements 6 are waved. Thereby, a high stability as well as a high elasticity of the resilient elements 6 may be achieved. Each of the resilient elements 6 comprises two ends 19, 20. The resilient elements 6 are connected to the member 8 at both of their ends 19, 20.

In particular, the resilient elements 6 form a clamp 25. The clamp 25 acts on the piston rod 3 from different sides of the piston rod 3 and, thereby, clamps the piston rod 3.

FIG. 6 shows a fifth embodiment of a drive assembly 1 for a medication delivery device. For clarity reasons, the piston rod is not depicted. The impeding element 2 comprises three resilient elements 6 comprising a meander shape. The resilient elements 6 are connected to the member 8 at both of their ends 19, 20. Furthermore, the resilient elements 6 are connected to each other. In particular, the resilient elements 6 form a clamp 25. The clamp 25 acts on the piston rod 3 from different sides of the piston rod 3 and, thereby, clamps the piston rod 3.

FIG. 7 shows a sixth embodiment of a drive assembly 1 comprising an impeding element 2. For clarity reasons, the piston rod is not depicted. The impeding element 2 is located at an opening 4 through which the piston rod 3 may extend. The opening 4 is formed by a member 8 which is permanently fixed to an outer housing of the medication delivery device. However, the shape of the shown impeding element 2 is not specific for the shown member 8. In particular, the shown impeding element 2 may alternatively be part of a dose limiting member 7 as shown in FIGS. 2A to 6 or of another member of the drive assembly 1.

The impeding element 2 comprises two resilient elements 6. In this embodiment, the resilient elements 6 are straight. The resilient elements 6 are arranged at opposite sides of the piston rod 3. In particular, the resilient elements 6 form a clamp 25. The clamp 25 acts on the piston rod 3 from different sides of the piston rod 3 and, and thereby clamps the piston rod 3.

The invention claimed is:

1. A drive assembly for a medication delivery device, comprising
   a piston rod movable from a start position to an end position for medication delivery and resettable from the end position to the start position, wherein
   the piston rod is configured as a lead screw, wherein the piston rod is configured to carry out a combined axial and rotational movement during movement from the start position to the end position, and
   an impeding element for impeding a movement of the piston rod from the end position to the start position during a reset of the piston rod, wherein the impeding element comprises at least one resilient element;
   a dose limiting member being configured to prevent the setting of a dose of medication which is larger than the maximal available amount of medication;
   wherein the impeding element is permanently fixed to an outer housing of the medication delivery device and is formed as an integral part of the dose limiting member.

2. The drive assembly of claim 1, comprising a plurality of resilient elements being located rotationally symmetric around the piston rod.

3. The drive assembly of claim 1, wherein the impeding element exerts a radial force on the piston rod.

4. The drive assembly of claim 1 comprising a member forming an opening, wherein the impeding element is located at the opening.

5. The drive assembly of claim 4, wherein the impeding element extends into the opening.

6. The drive assembly of claim 1 comprising at least one support bearing being configured to support the piston rod.

7. A medication delivery device comprising a drive assembly according to claim 1.

8. The medication delivery device of claim 7, comprising a medication receptacle which is configured to receive a cartridge containing a medicament.

9. The medication delivery device of claim 8, comprising a main body, wherein the receptacle is detachable from the main body to enable an exchange of the cartridge.

10. The medication delivery device of claim 9, comprising a locking device being configured to inhibit a movement of the piston rod towards a start position when the receptacle is attached to the main body.

11. The medication delivery device of claim 1, wherein the receptacle has to be detached from the main body to enable a reset of the piston rod.

12. The medication delivery device of claim 9, wherein the impeding element is configured to inhibit an unhindered resetting of the piston rod when the receptacle is detached from the main body.

13. A drive assembly for a medication delivery device, comprising:
   a piston rod movable from a start position to an end position for medication delivery and resettable from the end position to the start position, wherein
   the piston rod is configured as a lead screw, wherein the piston rod is configured to carry out a combined axial and rotational movement during movement from the start position to the end position,
   a member forming an opening through which the piston rod is disposed, and
   an impeding element for impeding a movement of the piston rod from the end position to the start position during a reset of the piston rod, wherein the impeding element,
      is located at the opening,
      comprises at least one resilient element, wherein the resilient member comprises a spring arm having a first end connected to the member and a second end protruding into the opening towards the piston rod; and
      is formed as an integral part of the member.

* * * * *